United States Patent
deSa et al.

(10) Patent No.: US 11,270,799 B2
(45) Date of Patent: Mar. 8, 2022

(54) IN-HOME REMOTE MONITORING SYSTEMS AND METHODS FOR PREDICTING HEALTH STATUS DECLINE

(71) Applicant: VINYA Intelligence Inc., Cleveland, OH (US)

(72) Inventors: Michael E. deSa, Rye, NY (US); Johnie Rose, II, Cleveland Heights, OH (US)

(73) Assignee: VINYA INTELLIGENCE INC., Cleveland, OH (US)

( * ) Notice: Subject to any disclaimer, the term of this patent is extended or adjusted under 35 U.S.C. 154(b) by 146 days.

(21) Appl. No.: 16/691,696

(22) Filed: Nov. 22, 2019

(65) Prior Publication Data
US 2021/0057101 A1  Feb. 25, 2021

Related U.S. Application Data (60) Provisional application No. 62/889,306, filed on Aug. 20, 2019.

(51) Int. Cl.
*G16H 50/30* (2018.01)
*A61B 5/00* (2006.01)
(Continued)

(52) U.S. Cl.
CPC .......... *G16H 50/20* (2018.01); *A61B 5/0022* (2013.01); *A61B 5/0205* (2013.01); *A61B 5/05* (2013.01); *A61B 5/112* (2013.01); *A61B 5/1102* (2013.01); *A61B 5/1115* (2013.01); *A61B 5/1116* (2013.01); *A61B 5/1118* (2013.01); *A61B 5/1126* (2013.01); *A61B 5/1128* (2013.01); *A61B 5/4812* (2013.01); *A61B 5/4833* (2013.01); *A61B 5/7264* (2013.01); *A61B 5/7275* (2013.01); *A61B 5/742* (2013.01);
(Continued)

(58) Field of Classification Search
None
See application file for complete search history.

(56) References Cited

U.S. PATENT DOCUMENTS 10,825,318 B1 *  11/2020  Williams ............... G06N 20/00
2003/0149367 A1 *  8/2003  Kroll .................... A61B 5/0205
600/483

(Continued)

OTHER PUBLICATIONS

Mueller et al., Liver stiffness: a novel parameter for the diagnosis of liver disease, May 24, 2010, Hepatic Medicine: Evidence and Research, 2010:12, 49-67 (Year: 2010).*

(Continued)

*Primary Examiner* — Janice A Mooneyham
*Assistant Examiner* — Karen A Hranek
(74) *Attorney, Agent, or Firm* — Marshall, Gerstein & Borun LLP (57) ABSTRACT

The present application relates generally to in-home monitoring and an early health crisis alarm system for elderly individuals and patients with chronic diseases. In one aspect, using artificial intelligence and signals from electricity usage, water usage, ballistocardiography (BGC), and ultra-wideband radar, the system and methods may be used to identify and track daily human activities and physical status in the home. Anomalies to patterns can be determined by identifying disruptions in previously established patterns.

23 Claims, 7 Drawing Sheets

(51) Int. Cl.
  *A61B 5/11* (2006.01)
  *G08B 21/04* (2006.01)
  *G16H 50/20* (2018.01)
  *G16H 40/63* (2018.01)
  *G16H 70/60* (2018.01)
  *G16H 20/30* (2018.01)
  *G16H 40/67* (2018.01)
  *G16H 10/60* (2018.01)
  *G16H 50/70* (2018.01)
  *G16H 20/10* (2018.01)
  *G06N 20/00* (2019.01)
  *A61B 5/0205* (2006.01)
  *A61B 5/05* (2021.01)
  *G06N 5/02* (2006.01)
  *G06Q 50/06* (2012.01)
  *G08B 7/06* (2006.01)
  *G16H 40/20* (2018.01)
  *A61B 5/024* (2006.01)
  *A61B 5/08* (2006.01)
  *G01R 15/18* (2006.01)

(52) U.S. Cl.
  CPC ............ *A61B 5/744* (2013.01); *A61B 5/746* (2013.01); *G06N 5/02* (2013.01); *G06N 20/00* (2019.01); *G06Q 50/06* (2013.01); *G08B 7/06* (2013.01); *G08B 21/043* (2013.01); *G08B 21/0423* (2013.01); *G08B 21/0453* (2013.01); *G08B 21/0484* (2013.01); *G08B 21/0492* (2013.01); *G16H 10/60* (2018.01); *G16H 20/10* (2018.01); *G16H 20/30* (2018.01); *G16H 40/63* (2018.01); *G16H 40/67* (2018.01); *G16H 50/30* (2018.01); *G16H 50/70* (2018.01); *G16H 70/60* (2018.01); *A61B 5/024* (2013.01); *A61B 5/0816* (2013.01); *A61B 2503/08* (2013.01); *G01R 15/18* (2013.01); *G16H 40/20* (2018.01)

(56) References Cited

U.S. PATENT DOCUMENTS

| | | | | |
|---|---|---|---|---|
| 2005/0278409 | A1* | 12/2005 | Kutzik | G16H 20/70 709/200 |
| 2008/0001735 | A1* | 1/2008 | Tran | A61B 5/7264 340/539.22 |
| 2008/0077020 | A1* | 3/2008 | Young | A61B 5/0205 600/484 |
| 2008/0117060 | A1* | 5/2008 | Cuddihy | A61B 5/1118 340/573.1 |
| 2016/0027278 | A1* | 1/2016 | Mcintosh | G08B 21/0423 715/741 |
| 2016/0212506 | A1* | 7/2016 | Norwood | H02J 13/0006 |
| 2016/0314255 | A1* | 10/2016 | Cook | G06N 20/00 |
| 2016/0378943 | A1* | 12/2016 | Vallee | G16H 10/60 705/2 |
| 2017/0004286 | A1* | 1/2017 | Gould | G16H 50/30 |
| 2018/0014772 | A1* | 1/2018 | Dolev | A61N 1/20 |
| 2019/0134096 | A1* | 5/2019 | Ilan | A61K 39/40 |
| 2020/0038671 | A1* | 2/2020 | Schulhauser | A61N 1/3904 |
| 2020/0098471 | A1 | 3/2020 | Ramakrishnan et al. | |
| 2020/0289033 | A1* | 9/2020 | Sivertsen | A61B 5/1117 |

OTHER PUBLICATIONS

Dunn et al., Frailty as Tested by Gait Speed is an Independent Risk Factor for Cirrhosis Complications that Require Hospitalization, Dec. 2016, The American Journal of Gastroenterology, vol. 111, 1768-1775 (Year: 2016).*
Rubio et al., Home monitoring of breathing rate in people with chornic obstructive pulmonary disease: observational study of feasibility, accesptability, and change after exacerbation, Apr. 20, 2017, International Journal of COPD 2017:12, 1221-1231 (Year: 2017).*
K Wlodzimirow et al., A systematic review on prognostic indicators of acute on chronic liver failure and their predictive value for mortality, Feb. 2012, Liver International, pp. 40-52 (Year: 2012).*
Berges et al., "User-Centered Nonintrusive Electricity Load Monitoring for Residential Buildings," Journal of Computing in Civil Engineering, Nov./Dec. 2011.
Brena et al., "Evolution of Indoor Positioning Technologies: A Survey," Journal of Sensors, vol. 2017, Mar. 29, 2017.
Britton et al., "Smart Metering as a Tool for the Remote Diagnosis of Leakage in Residential Households," Water, 2008.
Cook et al., "Mining the Home Environment," J Intell Inf Syst., vol. 43, pp. 503-519, 2014.
Dawadi et al., "Smar Home-Based Longitudinal Functional Assessment," Conference Paper, Sep. 2014.
Hsu et al., "Enabling Identification and Behavioral Sensing in Homes Using Radio Reflections," CHI, 2019.
Pinheiro et al., "Theory and Developments in an Unobtrusive Cardiovascular System Representation: Ballistocardiography," The Open Biomedical Engineering Journal, vol. 4, pp. 201-216, 2010.
Samimi et al., "A Review on the Rogowski Coil Principles and Applications," IEEE Sensors Journal, vol. 15., No. 2, 2015.
Sprint et al., "Detecting Health and Behavior Change by Analyzing Smart Home Sensor Data," IEEE International Conference on Smart Computing, 2016.

* cited by examiner

| Monitored Parameter | COPD | Heart Failure | Liver Disease | Multimorbidity | MCI | Traditional means of Monitoring | Passive Sensors |
|---|---|---|---|---|---|---|---|
| Respiratory Rate | ↑ | ↔ | ↑ | ↔ | — | Visiting nurse, wearable | UWB, BCG |
| Heart Rate | ↑ | ↑ | ↔ | ↔ | — | Wearable, implantable; Telemed | BCG |
| Toilet Flushes | — | ↓ | ↓ | ↔ | ↔ | Patient report | Water |
| Paroxysmal torso motion (Cough) | ↑ | ↑ | — | ↑ | — | Visiting nurse; Patient report | UWB |
| Use of specific medical devices | ↔ | ↔ | ↔ | ↔ | ↔ | Patient report; Telemed functions | Electricity |
| Night-time waking | ↑ | ↑ | ↑ | ↑ | ↑ | Patient report, Bed monitor | BCG, UWB, Electricity, Water |
| Sleep angle | ↑ | ↑ | — | ↑ | — | Patient report; Visiting nurse | BCG, UWB |
| Gait speed | ↓ | ↓ | ↓ | ↓ | ↓ | Wearable; Visiting nurse | UWB |
| Bed/chair-to-standing time | ↑ | ↑ | ↑ | ↑ | ↑ | Visiting nurse | UWB |
| Stair ascent/descent time | ↑ | ↑ | ↑ | ↑ | ↑ | Visiting nurse, wearable | UWB |
| Amount/speed of locomotion/(I)ADL's | ↓ | ↓ | ↓ | ↓ | ↓ | Patient report; Visiting nurse; wearable | UWB, Electricity, Water |
| Cooking | ↓ | ↓ | ↓ | ↓ | ↓ | Patient report | UWB, Electricity, Water |
| Eating | ↓ | ↓ | ↓ | ↓ | ↓ | Patient report; Visiting nurse | UWB, Electricity, Water |
| Bathing/showering -speed, frequency | ↓ | ↓ | ↓ | ↓ | ↓ | Patient report; Visiting nurse | UWB, Electricity, Water |
| Personal Hygiene (e.g. brushing teeth) – speed, frequency | ↓ | ↓ | ↓ | ↓ | ↓ | Patient report; Visiting nurse | UWB, Electricity, Water |
| Household chores (e.g. laundry, vaccum) | ↓ | ↓ | ↓ | ↓ | ↓ | Patient report; Visiting nurse | UWB, Electricity, Water |
| Home-leaving regularity | ↓ | ↓ | ↓ | ↓ | ↔ | Patient report; Door sensor | UWB, Electricity |

Fig. 6

IN-HOME REMOTE MONITORING SYSTEMS AND METHODS FOR PREDICTING HEALTH STATUS DECLINE

CROSS-REFERENCE TO RELATED APPLICATION

Under 35 U.S.C. § 119, this application claims priority to, and the benefit of, U.S. provisional patent application No. 62/889,306, entitled "REMOTE MONITORING SYSTEMS AND METHODS FOR ELDERLY & PATIENT IN-HOME CARE", and filed on Aug. 20, 2019, the entirety of which is hereby incorporated by reference.

BACKGROUND

The present application relates generally to remote in-home monitoring of elderly individuals and patients with chronic diseases.

Many elderly human subjects are aging-at-home alone, and in many situations suffer from one or more chronic diseases. These chronic diseases and conditions of aging require close monitoring by health professionals and family caregivers. Most of the prevailing methods of monitoring patients at home rely on fixed visiting nursing program schedules, telehealth, and/or wearable technologies that all have limitations. The healthcare system continues to face difficulties in predicting chronic disease exacerbation in the home, which leads to substantial stress and costs for the system and for patients and families. Furthermore, the ability to remotely manage patients with cognitive impairment is very limited due to the intermittent nature of data and inability to assess higher level function remotely.

An unobtrusive way to achieve remote patient monitoring is through sensor-enabled remote patient monitoring (RPM). There are several limitations to the prevailing knowledge and technologies that assist with RPM. For example, clinicians have limited insight into human subject behavior leading up to an event, relying largely on biometric or mobility data from worn sensors or subjective data from patients or caregivers. The technologies that monitor mobility or falls using worn devices are confronted by poor adherence and limited range coverage in the home. Additionally, most technologies do not allow tracking of markers of higher-level function including core daily activities of a human subject (such as eating, sleeping, bathing, toileting and walking in the home). Challenges of achieving such a comprehensive view of patient health status using currently available technology are heightened by issues of interoperability of sensor systems and intrusion.

The following provides new and improved systems and methods which overcome the above-referenced problems and others.

BRIEF DESCRIPTION

In one aspect there is a system for predicting an event for a patient comprising: the at least one processor; and the at least one memory including computer program code; at least one memory and computer program code configured to, with the at least one processor, cause the system at least to: receive at least one measurement from at least one sensor; determine an activity of the patient based on the received at least one measurement; and predict an event of the patient based on the determined activity.

In the system as described in the preceding paragraph, in some embodiments, the predicted event includes at least one of: chronic obstructive pulmonary disease (COPD); congestive heart failure (CHF); chronic liver disease (CLD); mild cognitive impairment (MCI); and multi-morbidity (more than one chronic condition). The determined activity may include one of: respiratory rate; heart rate; toilet flushes; paroxysmal torso motion; use of a medical device; night-time walking; sleep angle; gait speed; bed/chair-to-standing time; stair ascent/descent time; amount/speed of locomotion; cooking; eating; bathing/showering; personal hygiene; household chores; and home leaving regularity. In some embodiments, the at least one memory and the computer program code are further configured to, with the at least one processor, cause the system to determine the activity of the patient further based on: (i) ground truth observations, and (ii) training data from a home of the patient or from a population of patients. The activity may include a time the patient spends performing the activity. The system may further include: an audio alarm; wherein the at least one memory and the computer program code are further configured to, with the at least one processor, cause the audio alarm to emit an audible alarm if the predicted event is predicted to occur within a predefined time period. The system may further include: a visual alarm; wherein the at least one memory and the computer program code are further configured to, with the at least one processor, cause the visual alarm to emit a visual alarm if the predicted event is predicted to occur within a predefined time period. In some embodiments, the at least one sensor includes: a first electrical measurement device configured to continuously measure an overall power usage of a home of the patient; and a second electrical measurement device configured to continuously measure a power usage of a kitchen of the home. In some embodiments, the at least one sensor includes: a first electrical measurement device configured to continuously measure an overall power usage of a home of the patient, wherein the first electrical measurement includes a timestamp; a second electrical measurement device configured to continuously measure a power usage of a kitchen of the home, wherein the second electrical measurement includes a timestamp; a water sensor configured to generate a water usage measurement of the home, wherein the water usage measurement includes a timestamp; a vital sign sensor configured to measure a vital sign of the patent; a mobility sensor configured to measure mobility of the patient; and a presence sensor configured to measure a presence and respiratory rate of the patient. In some embodiments, the at least one memory and the computer program code are further configured to, with the at least one processor, cause the system to: predict the event based on a score calculated based on the determined activity and physical status; generate an amber alert if the score exceeds a first predetermined threshold; and generate a red alert if the score exceeds a second predetermined threshold. In some embodiments, the system further includes: a water sensor configured to measure toileting of the patient; and a respiration sensor configured to measure a respiration rate of the patient; wherein: the event is chronic obstructive pulmonary disease (COPD); and the at least one memory and the computer program code are further configured to, with the at least one processor, cause the system to predict the COPD event based on the respiration rate of the patient but not the toileting of the patient. In some embodiments, the event is liver disease, and the at least one memory and the computer program code are further configured to, with the at least one processor, cause the system to predict the liver disease event based on a gait speed of the patient but not the sleep angle of the patient.

In the system as described in either of the preceding paragraphs, the predicted event may include chronic obstructive pulmonary disease (COPD); the at least one memory and the computer program code are further configured to, with the at least one processor, cause the system to receive one-way information from a medical device, and predict the event further based on the signal received from a medical device. The predicted event may include congestive heart failure (CHF); and the at least one memory and the computer program code are further configured to, with the at least one processor, cause the system to predict the event further by applying an anomaly detection machine learning method to a signal received from a cardiac defibrillator or pacemaker. The predicted event may include chronic liver disease (CLD). The predicted event may include chronic liver disease (CLD); and the at least one memory and the computer program code are further configured to, with the at least one processor, cause the system to predict the event further by applying an anomaly detection machine learning method to a signal of a liver stiffness or liver steatosis. The predicted event may include mild cognitive impairment (MCI); and the at least one memory and the computer program code are further configured to, with the at least one processor, cause the system to predict the event further by applying an anomaly detection machine learning method to an integrated data stream from a neural stimulator device that stimulates brain memory function. The predicted event may include Multi-Comorbidity; and the at least one memory and the computer program code are further configured to, with the at least one processor, cause the system to predict the event further by applying an anomaly detection machine learning method to a signal received from a medical device. The predicted event may include chronic disease exacerbation or health status decline disease-agnostic.

In another aspect, there is a method, comprising: receiving at least one measurement from at least one sensor; determining an activity of the patient based on the received at least one measurement; and predicting an event of the patient based on the determined activity.

In yet another aspect, there is a system for determining an activity of a patient comprising: at least one processor; and at least one memory including computer program code; the at least one memory and the computer program code configured to, with the at least one processor, cause the system at least to: receive at least one measurement from at least one sensor; and determine the activity of the patient based on: (i) training data from a population of patients and/or training data from a home of the single monitored patient, and (ii) the received at least one measurement from the at least one sensor; wherein the activity includes at least one of: a common daily activity; an activity of daily living (ADL); chronic obstructive pulmonary disease (COPD); congestive heart failure (CHF); chronic liver disease (CLD); mild cognitive impairment (MCI); and Co-Morbidities.

In the system as described in the preceding paragraph, the at least one sensor may include a ballistocardiograph (BCG) measurement device. In some embodiments, the at least one sensor includes an ultra-wideband (UWB) radar, and the at least one measurement includes a presence and respiratory measurement. In some embodiments, the at least one sensor includes an ultra-wideband (UWB) radar, and the at least one measurement includes a respiratory rate and heart rate measurement. In some embodiments, the at least one memory and the computer program code are further configured to, with the at least one processor, cause the system to determine the activity of the patient further based on ground truth observations.

In the system as described in either of the preceding paragraphs, the at least one memory and the computer program code may be further configured to, with the at least one processor, cause the system to determine the activity of the patient by labeling machine learning models of prediction of identified behavior. The training data may comprise data acquired with in a two week time period. The system may further comprise a dashboard, and wherein the at least one memory and the computer program code are further configured to, with the at least one processor, cause the system to: display an avatar of the patient on the dashboard; and display a three-alarm system on the dashboard. The system may further comprise a dashboard configured to connect to end user health record systems and into mobile applications. The system may further comprise a hub configured for edge processing. The at least one sensor may include an electrical sensor, and the at least one measurement includes an electrical measurement from the at least one electrical sensor; the system further includes a load identifier configured to receive electrical measurement and disaggregate the electrical measurement; the at least one memory and the computer program code are further configured to, with the at least one processor, cause the system to determine the activity based on the disaggregated electrical measurement. The system may further comprise a water sensor configured to measure water usage of the home; the at least one memory and the computer program code are further configured to, with the at least one processor, cause the system to determine the activity based on the measured water usage. The system may further comprise a dashboard configured to connect to a wearable. The system may further comprise a dashboard configured to connect to a smart speaker. In some embodiments, the activity is a common daily activity. In some embodiments, the activity is ADL One advantage resides in an in-home patient monitoring system that operates without the use of microphones, cameras, or other data gathering with the potential to allow direct identification of home occupants.

A second advantage of the systems and methods described herein is that patients may be monitored without the use of wearable devices or implants—removing patient and family caregiver adherence as a barrier to effectiveness. For patients who are monitored by such worn and or implanted technologies, the systems and methods described herein provide complementary functions.

Other advantages will become apparent to one of ordinary skill in the art upon reading and understanding this disclosure. It is to be understood that a specific embodiment may attain, none, one, two, more, or all of these advantages.

The invention may take form in various components and arrangements of components, and in various steps and arrangements of steps. The drawings are only for purposes of illustrating the preferred embodiments and are not to be construed as limiting the invention.

DETAILED DESCRIPTION

Hardware Architecture. The following will illustrate an example implementation of the systems and methods described herein.

Figure 1A:
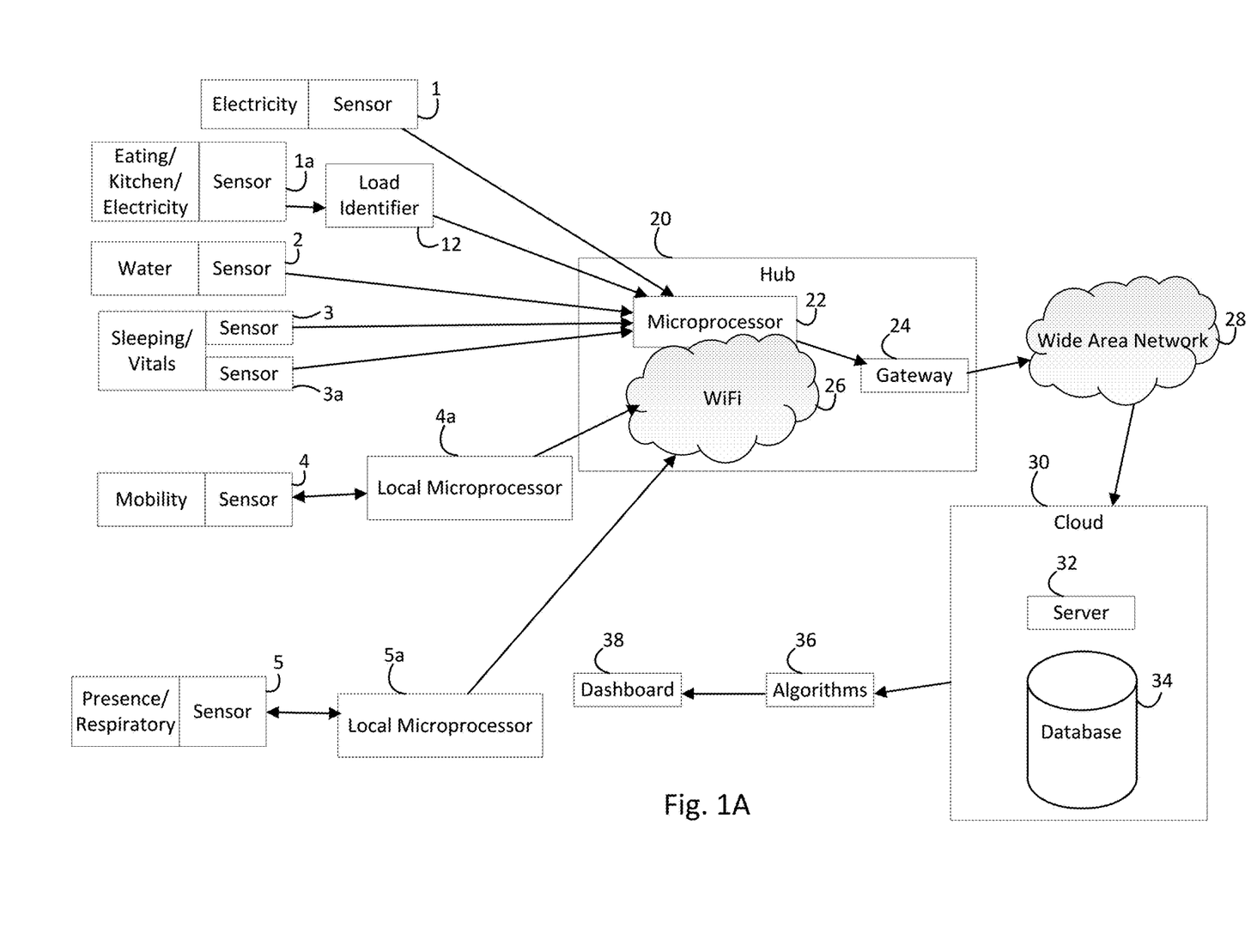
FIG. 1A is a block diagram of an exemplary integrated and interoperable contactless sensor architecture with an embedded gateway (hub) that communicates with a server where processing develops an actionable user interface/data dashboard.
Figure 5:
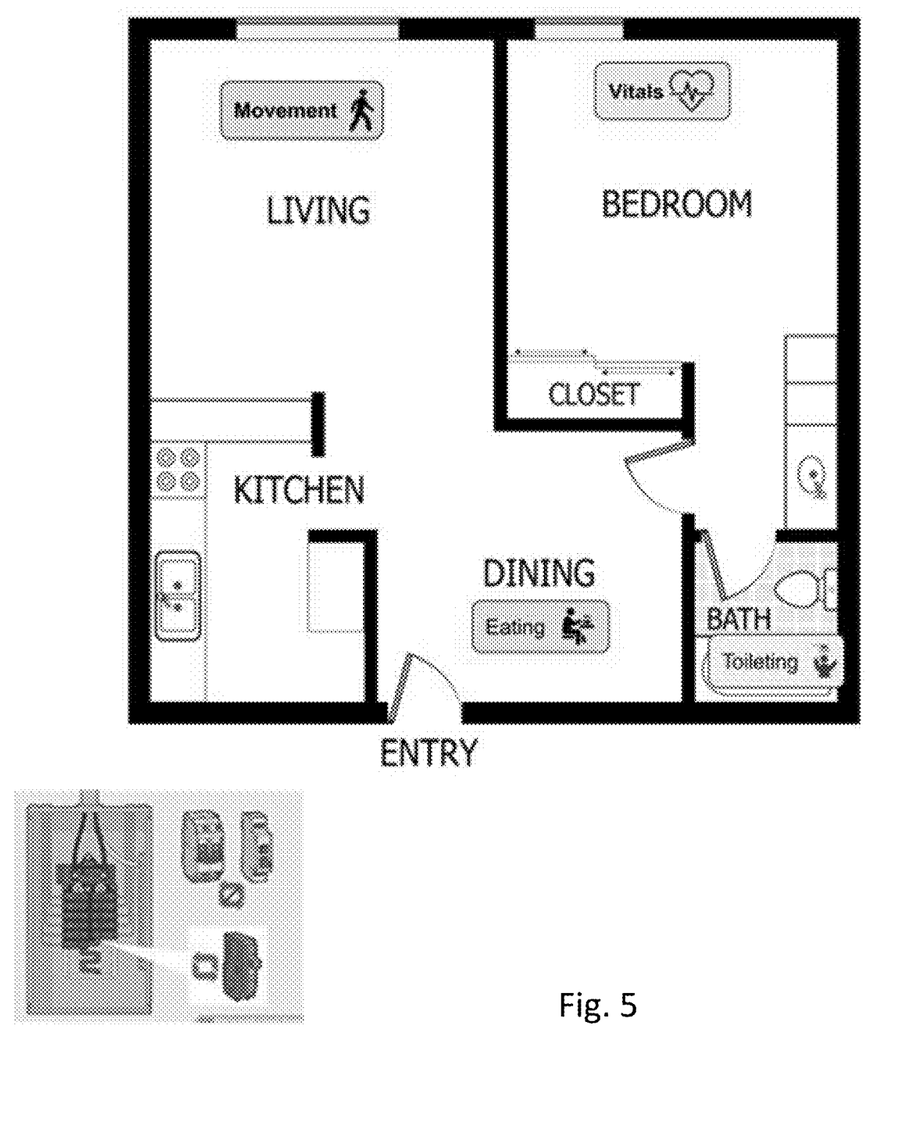
FIG. 5 illustrates an example dwelling that may be equipped with the systems and methods described herein.

With continuing reference to the example of FIG. 1A, a hardware engineering system includes sensors 1, 1a, 2, 3, 3a 4, 5, and a home-hub product that transmits processed and unprocessed data to backend servers embedded with proprietary software systems. The installation occurs in a customer home, which, in some examples, may be a single family, town house, apartment or suite with a standalone electric circuit breaker management system (see, e.g., FIG. 5). The installation may or may not require a certified electrician and can often be completed in under two hours. The engineering architecture includes electrical current transformer system; ultrasound acoustic water system; a sleeping, respiratory and heart rate monitoring system; a mobility tracking system; presence sensor; local microprocessors; a load identifier system; a local Wi-Fi system and communications gateway (LTE-M or NB-IoT) embedded in a hub with a microprocessor; a wide area network to enable distributed data management; remote servers; algorithms; and a dashboard. There are five core sensors used, and they are controlled by a single home-hub which is comprised of a microprocessor and wireless communication gateway. The technology applied in this application is contactless and passive, and does not require cameras or any form of personal interaction with digital assistants, wearables (e.g. Apple watch or FITBIT), or telemedicine devices.

The following will now describe sensors used in the systems and methods of the present application. It should be understood that the term "sensor" may refer to a single sensor, or to a grouping of sensors that are the same or different kind of sensors. For example, sensor 1 may refer to a single electrical sensor, or to multiple electrical sensors placed in the house. In another example, sensor 4 may refer to a grouping of sensors that includes both an ultra-wideband radar unit as well as a piezoelectric sensor.

Sensor 1 is an electrical sensor. In one implementation, sensor 1 is a set of electro-magnetic current transformer rings that are located on the main load center electrical panel of the home. These can be located either at specific circuit breakers that are being monitored or at the main electric lines entering the load center. The system has a set of algorithms that enables the identification of specific appliances, lights, or other devices connected to the home's electrical system based on characteristic patterns of current and resistance.

Sensor 1a is a subset of electro-magnetic current transformer rings that are located on the circuit breakers related to the kitchen. The circuit breaker load identification algorithms permit usage tracking at the unit level (e.g. microwave, refrigerator, electric kettle). The sensor 1a does not have a battery and connects through local embedded Wi-Fi to the hub. These high-resolution technologies will measure the use of specific electrical devices (e.g. HVAC, refrigeration, plug loads) through an electric load disaggregation model.

Sensor 2 is a water sensor that may be located on the home's main water supply line near where it enters the home; the line can be either PVC material or metal. Sensor 2 applies an inaudible ultrasound acoustic measuring methodology to ascertain the flow rate of water drawn down over time. The algorithms are designed to learn how to attribute patterns of water flow and volume to specific fixtures and activities (e.g. toileting in a particular bathroom, bathing, running dishwasher). Sensor 2 connects locally through Wi-Fi embedded to the hub and, in some embodiments, does not operate with batteries. This non-invasive sensor technology does not necessitate cutting pipes or wires and does not rely on utility provider participation.

Figure 3:
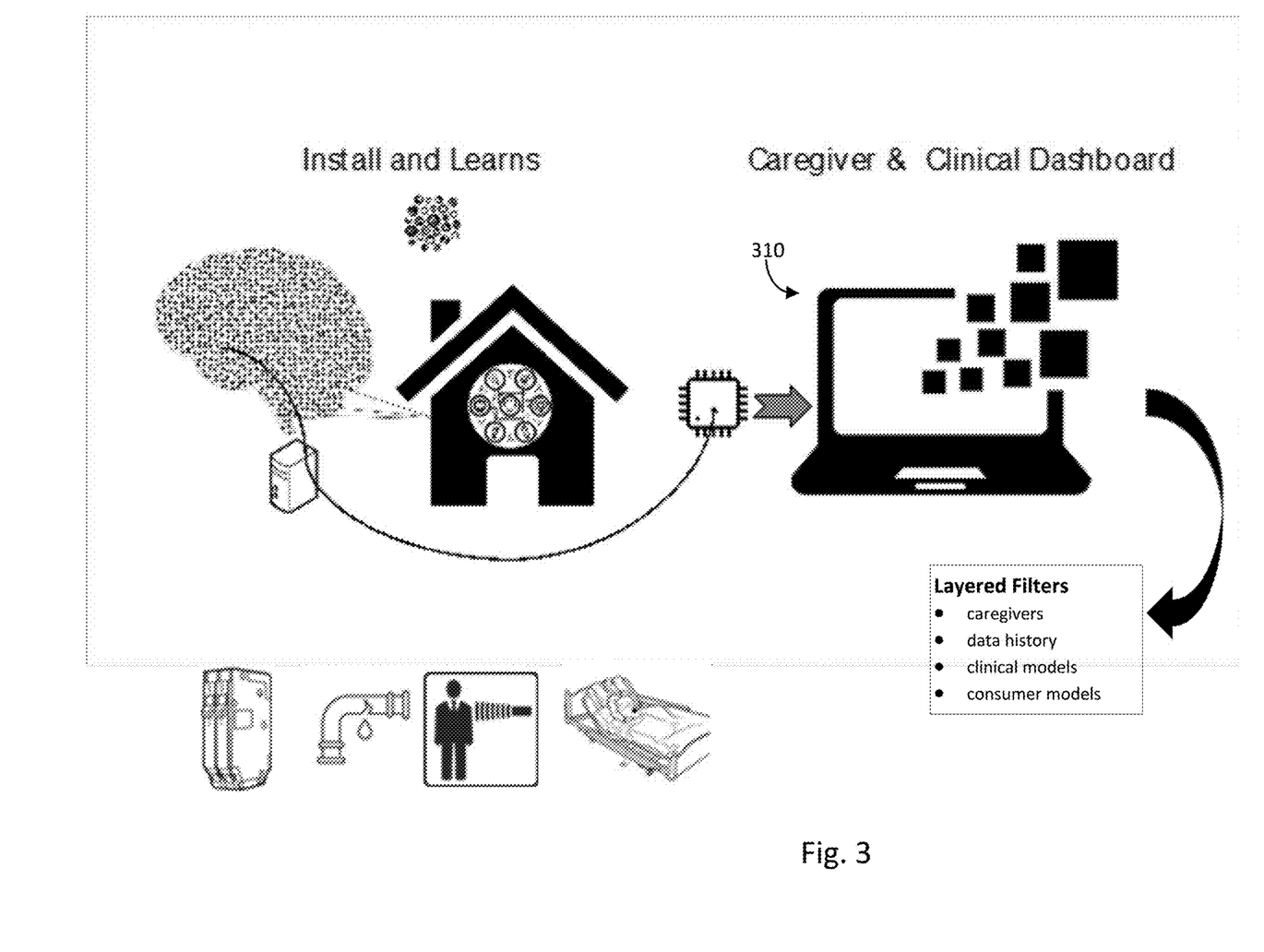
FIG. 3 illustrates a schema of tiered data accessibility for monitored subjects, doctors, nurses, caregivers, insurers, medical device controllers, digital assistants, telehealth systems, home-healthcare services, and so forth.

Sensor 3 is a signal sensor that is located between the mattresses of the bed (this is also illustrated in FIG. 3). In one implementation, sensor 3 is a piezoelectric sensor that converts mechanical stress into electrical signals. In some embodiments, the sensor 3 may include a camera(s); in some embodiments, the sensor 3 does not include any cameras. The system may use a ballistocardiograph (BCG) method, which is a non-invasive method that is based on the measurement of the body motion generated by the ejection of the blood at each cardiac cycle and movement of the chest wall associated with respiration. The system uses the information from sensor 3 to define periods of sleep as rapid eye movement (REM), deep, and light phases based on heart rate, respiratory rate, and gross movement. There is one sensor required (although more may be used) which can be located in proximity to the monitored human even if the bed has two occupants. Sensor 3 may be connected locally to a power receptacle and, in some embodiments, does not operate on batteries.

Further regarding sensor 3, the aggregated sensor data from the same bed sensor produces respiratory rate (RR) and heart rate (HR) measurements using a set of algorithms. This method measures the mechanical aspects of respiratory activity through chest wall movement, and of heart activity through movements produced by ejection of blood from the heart into the great vessels. Accordingly, the system can produce a set of vital signs on an interval basis. In some embodiments, the sensor does not have a battery and connects through a local microprocessor to the hub.

Sensor 3a, in some embodiments, is a piezoelectric and BCG sensor that measures vital sign information. In some embodiments, sensor 3 performs two functions: a) sleep monitoring, and (b) respiratory rate and heart rate monitoring.

Sensor 4 is a three-dimensional (3D) mobility sensor. In one embodiment, this sensor uses ultrawideband radar to track the mobility of the human. It is a 3D sensor that emits ultrawideband radar waves and senses waves which are reflected from objects. The energy used will penetrate most building walls. In some embodiments, the single sensor is positioned to maximize its coverage area of at least 300 square feet and capture relevant mobility. In some embodiments, it does not operate on batteries and connects through a local microprocessor to the hub. The UWB radar sensor uses radio wave reflections to collect position, mobility, and gait information on a human in an indoor environment, even when the person may be in another room from where the device is located.

Sensor 5 combines two high-resolution sensors that use ultra-wideband (UWB) radar with BCG to track presence and respiratory rate (RR) (e.g. sensor 5 may include an ultra-wideband radar unit as well as one or more piezoelectric sensors for the BCG). The UWB radar sensor uses radio wave reflections to collect position, mobility, and gait information on a human in an indoor environment, even when the person may be in another room from where the device is located BCG is a technique for detecting motion of the human body including that from the sudden ejection of blood into the great vessels with each heartbeat or chest wall movement associated with respiration.

Sensor 5 is able to measure the respiration rate with high accuracy, and overall deliver data comparable to polysomnography. The sensor provides advanced respiration and presence tracking both during the day and throughout the night. In some embodiments, the programmable detection ranges up to 5 meters is a key feature for the sensor. It allows non-contact, high accuracy monitoring of respiration, presence and movement in a room. The sensor is an ultrawide band (UWB) impulse radar transceiver chip that senses movement at distances up to 5 meters and operates at sub 10 GHz frequencies.

Local microprocessors 4a and 5a are programmed to combine and process data emanating from sensor 4 (microprocessor 4a) and sensor 5 (microprocessor 5a) and relay to the hub via Wi-Fi 26 embedded in its system at a specified frequency. The gateway hub 24 uses either a NB-IOT or LTE-M sim card or a highspeed data router to transmit data to the server 22; this functionality can be switched off. The data can also be transmitted to separate gateway routers concurrently through two dedicated chips in the local microprocessor if the optionality is exercised. Although the example of FIG. 1A shows Wi-Fi 26, it should be understood that local communication, in some embodiments, may occur via any communication medium (e.g., a Wi-Fi Network, any type of LTE network, a Zigbee network, and so forth).

Load Identifier 12 pushes aggregated data from sensor 1, sensor 1a, and sensor 2 through a load identifier inbuilt microprocessor via Wi-Fi to the hub. The disaggregated electrical load and water flow data is processed to identify the use of individual devices and fixtures at the load identifier 12 level on the remote server. Once it passes through the gateway to a remote server, it undergoes further machine learning to increase validation, classification and attribution.

Hub 20 is a hardware container unit comprised of a microprocessor 22 and a communications gateway 24. The hub 20 integrates aggregated data from the sensors 1, 1a, 2, 3, 3a, 4, and 5, as well as the microprocessors 4a, 5a by reading the data at different time intervals. The hub 20 also pushes raw and processed data via the gateway 24 to a remote server 32 through an external wide area network 28. The hub 20, in some embodiments, provides edge processing, memory, two-way Wi-Fi, and a gateway comprised of narrow band Internet of things (NB-IoT) and long-term evolution for machines (LTE-M) broadband interface to the remote server in the cloud.

Cloud 30 comprises a dedicated remote server 32 located in a secure controlled storage environment. The data is processed into structured and semi-structured data elements in the database 34 and is made available for applied algorithms to create the output of labelled daily living activities and identification of changes/anomalies in activities, vital signs, and sleeping over time which are associated with chronic disease exacerbations.

Dashboard 38 receives 24 hour×7 days a week early warning system alerts from the database 34 (through algorithms 36), and the data is subsequently converted into separate layered visualizations for caregivers and clinicians in the form or red/amber/green signals (e.g., a three-alarm system) representing levels of alert, concern, and no concern, respectively. This triaging is based on probability of unscheduled utilization of emergency or inpatient healthcare services in the next 24-72 hours. The dashboard may include an avatar (e.g. a representation of a character such as the patient or a caregiver).

Figure 1B:
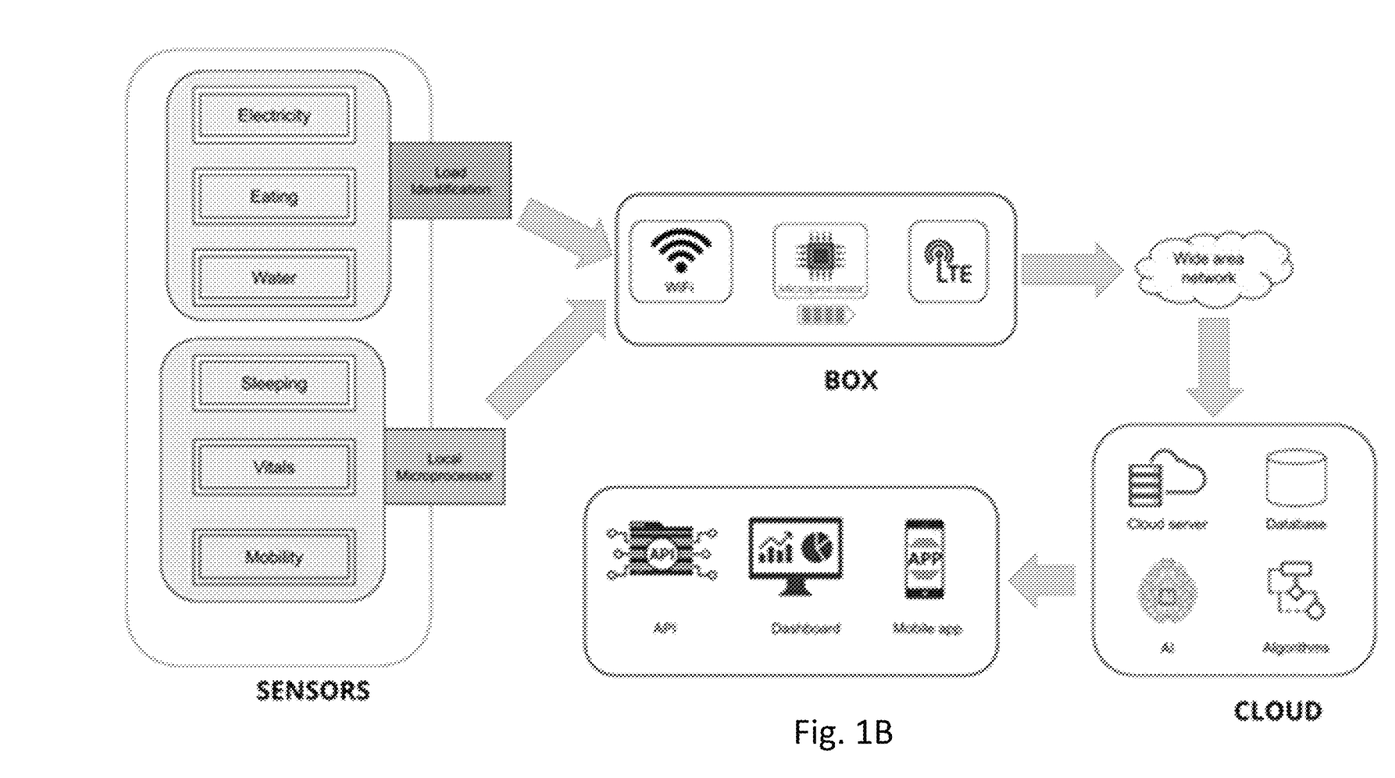
FIG. 1B is a block diagram of an alternative exemplary integrated and interoperable contactless sensor architecture with an embedded gateway (hub) that communicates with a server where processing develops an actionable user interface/data dashboard.

FIG. 1B is a block diagram of an alternative exemplary integrated and interoperable contactless sensor architecture with an embedded gateway (hub) that communicates with a server where processing develops an actionable user interface/data dashboard.

Exemplary System Elements

Figure 4:
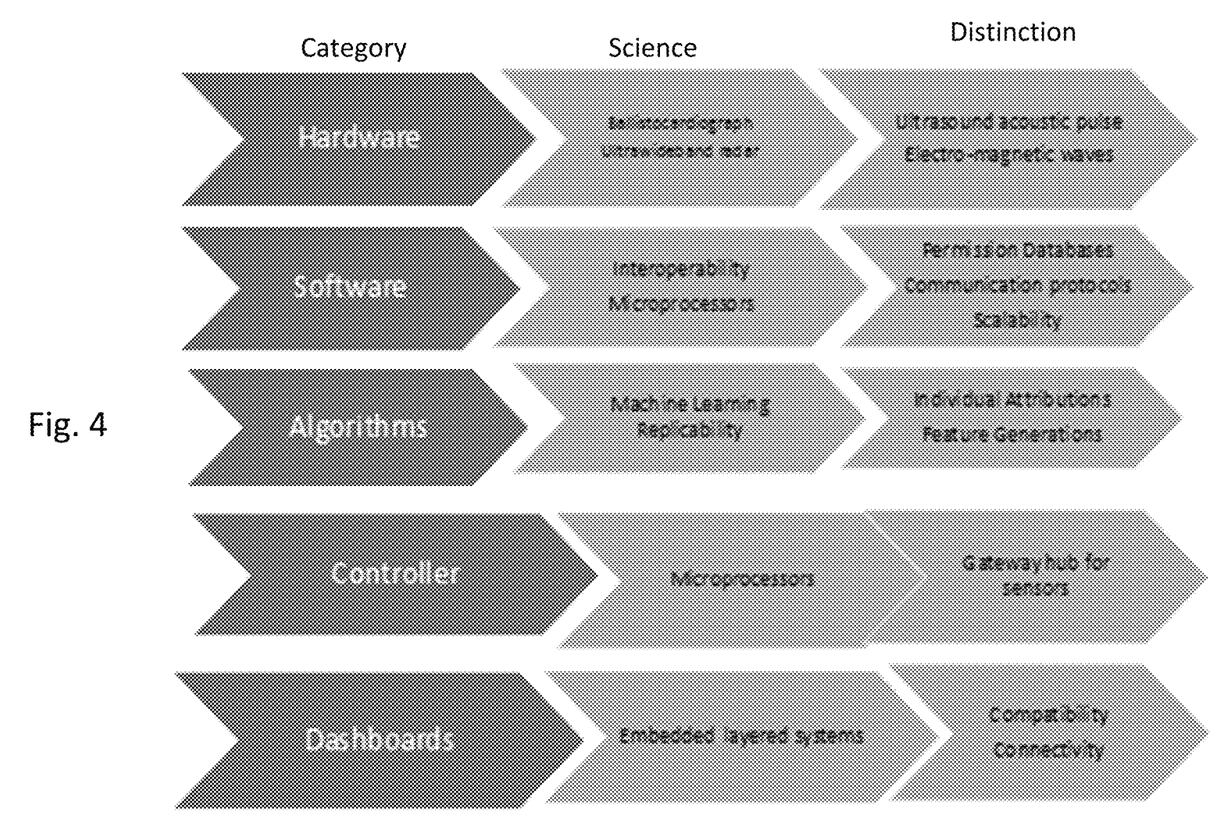
FIG. 4 illustrates five distinct processes related to the hardware, software, controller hubs, algorithms, dashboards and gateways.

FIG. 4 illustrates five distinct processes related to the hardware, software, controller hubs, algorithms, dashboards.

Exemplary hardware is based on a set of four underlying sciences (electricity, water, BGC, and ultra-wideband radar) that have been proprietarily selected for an optimum level of adoptability, scalability and validity. In the case of electrical usage and load disaggregation, research has validated energy efficiency models through electrical non-intrusive load monitoring of residential buildings. (Berges, Goldman, Matthews, Soibelman, & Anderson, 2011; Zoha, Giuhak, Imran, & Rajasegarar, 2012). Non-intrusive electric load is monitored through electro-magnetic waves enabled with Rogowski coils that are embedded in current transformer sensors and located in the circuit breaker board. (Samimi, Mahari, Farahnakian, & Mohseni, 2014). To ascertain disaggregated water usage, non-invasive inaudible ultrasound acoustic & vibration pulse waves are applied to measure rate of water flow. (Britton, Cole, Stewart, & Wiskar, 2008). In some embodiments, to monitor the mobility of a human subject in the home, an application of 15-18 antennas ultra-wideband Radio Frequency (RF) tridimensional (3D) sensing and image processing is installed. (Brena et al., 2017). The antenna array illuminates the area in front of it and senses the returning signals. The signals are produced and recorded by an integrated circuit chip and the data is communicated to the remote server via the hub gateway 24. To monitor sleep, heart rate (HR) and respiratory rate (RR), the ballistocardiograph method (BCG) is applied and measures sleep stages based on heart rate, respiratory rate, and gross movement. Ballistocardiography measures movements linked with cardiac contraction & ejection of blood and with the deceleration of blood flow through blood vessels. (Pinheiro, Postolache, & Girão, 2010). Chest wall and gross movements are also detected through this method.

The controller hub 20 combines hardware and software to enable distinct capabilities and processes in various implementations. This is a distinct home hub that integrates and enables the interoperability of the sensors. In some embodiments, the microprocessor 22 is a quad core microprocessor. The microprocessor 22 may combine a single 802.11n (2.4 GHz) wide coverage WiFi low power chip with 4G LTE-M Internet connectivity, allowing the system to reliably transmit data. It has multiple power modes and provides dynamic power scaling. It integrates an antenna switch, radio frequency, power amplifier, filters and other power management modules. The hub 20 is embedded with a communications gateway 24 that transmits data to an external server 32. Data is read from the IoT sensors on a proprietarily defined time interval-based system that relies on degree of relevance, which changes dynamically. The interrogation of each sensor differs by sensor based upon relevance and human subject conditions; thus, it can stream data in batches at intervals ranging from seconds to 12-hours; this rate can vary within its sub-components. The hub 20 has the capability of transmitting raw sensor data to the remote server 32 through the communications gateway 24 or processing the raw sensor data locally (at the "edge") to transmit data which has been partially or fully transformed for input into algorithms. Whether edge processing occurs may change dynamically based on human subject health.

Regarding gateway communications, the hub 20 provides edge processing, memory, two-way WiFi, and a gateway interface comprised of narrow band Internet of things (NB-IoT) and long-term evolution for machines (LTE-M) broadband interface to the remote server in the cloud. NB-IoT is a low power wide area technology that enables the sensor to improve power consumption and spectrum efficiency. This new physical layer signal can provide extended coverage into deep indoors environments with ultra-low device complexity. The LTE-M optimally addresses the low-powered sensors being used.

The application combines standards of IEEE 802.11, that include WIFI®, ZigBee, Z WAVE®, BLUETOOTH®, local area network (LAN) including using Ethernet and wide area networks (WAN). All data packets have unique encrypted security codes that cannot be deciphered and protect human subjects' information.

Software: The software code creates a distinct set of processes that enables the hub platform to operationalize an interoperable sensor system across water, electricity, vital signs, and human body actions. Programming languages and formats used are Java, Java Script, C++, Python. The use of JSON (Java Script Object Notation) is applied by using readable text to transmit data objects and the use of nodeJS, which is an event architecture capable of optimizing throughput and scalability. These communication protocols are programmed in Java Script and no user interface is permitted with the proprietary hub. The hub 20 is encrypted and HIPAA (Health Insurance Portability and Accountability Act) compliant and does not provide raw sensor data to any external entity or individual. The remote server 32 is located in the cloud 30, and uses NO-JS as an open source cross-platform to execute its Java Script programming functions. A set of distinct code is used to integrate individual sensors to related microprocessors. A back-end program function to receive, validate, organize, and store data is conducted in the server to transform the raw-sensor data into structured and semi-structured formats (data elements) and sent to the database 34 where it can be accessed by registered internal individuals. The database 34 linkages are made available to authorized desktops for data engineering and data science processes. In one implementation, the database 34 is a MongoDB®. MongoDB® is a document database with the scalability and flexibility that permits querying and indexing. The platform has strict data encapsulation, meaning there are several layers built in that enforce limited access to data. All external access is mediated through our application programming interface (API), where we have implemented security and audit checks to authenticate access to data.

Figure 2:
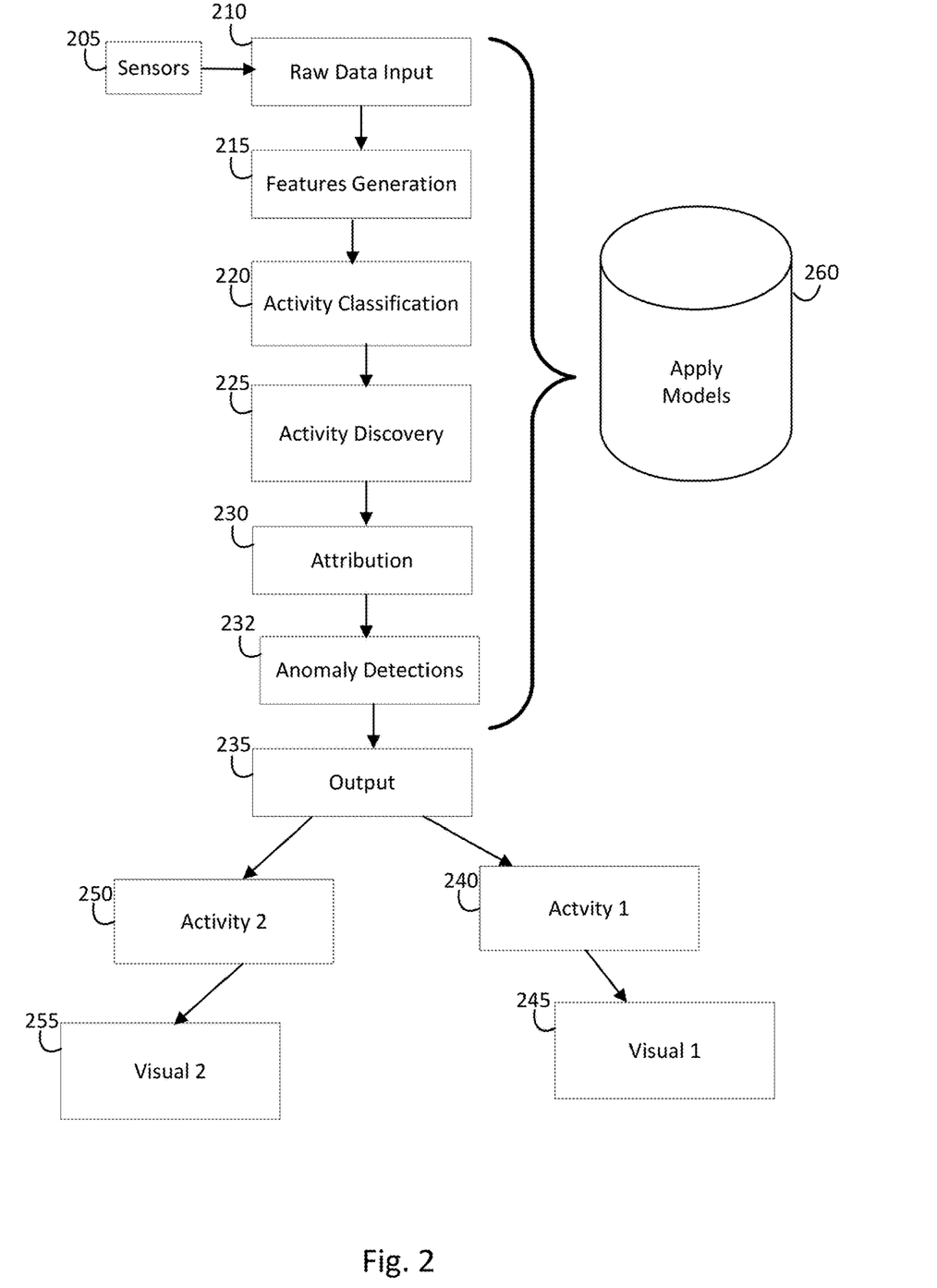
FIG. 2 is a block diagram of an exemplary data engineering and data science process that applies a set of distinct data processing or analysis algorithms at each separate stage from raw data input to the output of actionable steps delivered through a user interface visualized as a dashboard.

Algorithms: Research has validated that behavioral activities are detected through Passive Infrared Sensors 205 and are predictive of health deterioration in seniors (Cook, Krishnan, & Rashidi, 2013; Dawadi, Cook, & Schmitter-Edgecombe, 2016; Sprint, Cook, Fritz, & Schmitter-Edgecombe, 2016). FIG. 2 represents the algorithmic methods utilized to collect and process raw input data 210 that are read from the sensors 205. At the raw data stage of the hub 20 the microprocessor 22 has built-in algorithms that dynamically change based on the anomalies of the human's daily living activities. As raw data arrives into the remote server, the code implements selected algorithms to determine the structured and semi-structured data types that are required to develop the optimal output results. Structured data is a data whose elements are addressable for effective analysis. It includes all data which can be stored in database SQL in table with rows and columns, that have relational keys, that can easily be mapped into pre-designed fields, and that are an example of relational data. Semi-structured data is information that does not reside in a relational database but that has some organizational properties; an example is tags and markers that make it easier to analyze. With some process, this data can be stored in the relational database. An example of this is XML data.

Based on health conditions, these algorithms are adjusted dynamically; for example, the models may be "tuned" or further trained. Several standard machine learning methods are applied and non-standard models to develop feature generation 215, activity classification 220, activity discovery 225, and human subject attribution 230 before the output 235 is developed that related to routine activities 240, 250 and anomaly detections 232. Visuals 245, 255 may be created based on the activities 240, 250. Support vector machine, logistic regressions, random forest, sequential pattern mining and convolutional neural network methods are applied within a set of model metrics that is depended on individual health conditions.

Neural network (specifically Long Short-Term Networks) and deep learning models are continually updated with time series inputs of labeled activities, mobility measures, discovered activities sequences, and vital signs. These models identify significant changes in these inputs over time, allowing the recognition of anomalous activity on the part of the monitored individual.

The example of FIG. 3 shows an embedded, layered system of information and visualization. The healthcare provider, patient, is provided access to patterns of daily living activities on the dashboard 310 and this information is available to caregivers as well. In some embodiments, the patient cannot tamper with any of the technologies with exception of the bed sensor (e.g., sensor 3 of FIG. 1A), which provides the individual optionality to switch on/off the power source to the bed sensor. The dashboard's layered system provides insight into daily routine of living activities, history of specific activities and related anomalies, and vital signs of heart rate (HR) and respiratory rate (RR) as well as vital sign histories. An algorithm creates a layered alarm system of alerts via the dashboard from low-threshold signals to caregivers and high-threshold alerts to healthcare professionals. The human subject is not required to activate any alarms. Furthermore, the dashboard can be integrated into family member phone IoS and Android based systems and also into the electronic health record systems, e.g. EPIC and CERNER-GENESIS, wearables and smart speaker systems.

Exemplary Process

"HUB" Hardware & Software Engineering: In the example of FIG. 1A, the microcontroller located in the hub 20 has one LED window to enable assessment and trouble shoot from readings within the hub 20. A python language-based software program is coded to read data from Sensor 4 (and microprocessor 4*a*) and uses WebSocket to secure handshake protocols and then transmits data to the external server in a JSON format. WebSockets are used to connect and send data and provide full duplex communication with the server and has speeds of up to twice those of REST APIs. The over the air (OTA) protocols are established to permit remote monitoring and updates. Similarly, sensor 4 data are read by the microcontroller 22 located in the hub 20, and the sensor receives commands from WebSockets to transmit data to servers. Sensor 1, 1a, and 2 have independent application programming interfaces (APIs), which permit "crawling" at a frequency based on our models. A "crawler" is best described as a program that simulates the user's behavior on a website, following all the steps a user does with the browser such as entering search parameters (e.g. destination, date, etc.), requesting a result by clicking on the search button and then scanning through them. In addition, a REST API server is established to receive crawled data to provide flexibility. In some embodiments, the remote server uses a MongoDB® which is controlled by an administrative panel that permits users to create and download .csv files of structured and semi-structured data. The home hub 20 is a container that co-locates a microprocessor 22 and communications gateway 24. The distinct feature of the hub 20 and its related micro-processor is the ability to integrate, control and enable the interoperability of four different sciences (electricity, water, BGC, and ultra-wideband radar); it enables edge computing, and produces time series histories of at least six common activities (eating, sleeping, bathing, toileting, walking, and cooking). The software program controls the sequencing of each data input to generate a value-based structure to enable predictive modeling. The hub has an in-built gateway that can adopt a low capacity or high capacity data router using either NB-IoT, LTE-M or others, these routers can also be programmed to shut down so that the hub can be connected to third party gateways. Table 1 below identifies the programming languages that are associated with each hardware unit within a context for a specific purpose and the type of output and related value it provides.

TABLE 1

| PURPOSE | CONTEXT | INPUT | LANGUAGE | FEATURES |
|---|---|---|---|---|
| monitoring movement | home | Ultrawideband radar sensor | Python/C++/ algorithms | health alert health assessment |
| monitoring water usage | home | ultrasound acoustic sensor | Python/ algorithms | home risk health assessment |
| Monitoring cooking & eating | residence kitchen | electromagnetic signals sensor | Python/ algorithms | health assessment home risk |
| monitoring RR/HR | subject's bed | ballistocardio-graphy sensor | Python/C++/ algorithms | Clinical management health data |
| monitoring sleeping | subject's bed | ballistocardio-graphy sensor | Python/C++/ algorithms | health assessment health data |
| caregiver & clinical monitoring | home | integrated sensors | NoJS/ algorithms-JSON | Dashboard |
| Hub controller | home | Integrate sensors Pull/push data | C++/Python | interoperability |
| Remote Server | remote | Pull data | Java Script/ algorithms | data security |

Algorithms: FIG. 2.

Summarizing features are generated from raw sensor inputs. These features serve as inputs to classification algorithms which label characteristic patterns of features as certain daily activities (e.g. bathing, toileting, cooking, etc.). Classification approaches utilized include support vector machines, logistic regression, and random forest models; to provide the most robust classifications, some embodiments use a model fusion technique to create a single label from the combined outputs of each model type. In parallel, raw sensor inputs feed a sequential pattern mining algorithm which recognizes, but does not label, similar sensor sequences. Labeled activities and stereotypical unlabeled sequences are probabilistically attributed to individuals in a multi-occupant dwelling based on location in the dwelling, body habitus, and/or gait characteristics.

Sensor windows—Because the streams of sensor data to be categorized are continually flowing, a method is needed to define a discrete series of contiguous sensor events for analysis. Some embodiments use a sliding window method which an activity window $S_i$ containing N sensor events is defined by sensor event i and the N−1 sensor firings preceding it. A sliding window method refers to the number of observations recorded for a given time window in a time series dataset. Each activity window has an associated "feature vector", which contains the time of the first sensor event $s_1$, the time of the last sensor event $s_i$, and one element for each sensor in the home describing the number of times each respective sensor has fired during window $S_i$. A feature vector is an n-dimensional vector of numerical features that represent an object. Because a given window (with length defined by number of sensor events) may encompass sensor firings from different functional areas of the home over different time intervals, the influence of more physically remote sensors will be discounted based on the mutual information method outlined by Krishnan and Cook. A mutual information matrix describing the extent to which all possible pairs of sensors are activated simultaneously, an example is adjacent sensors will be most closely related, and will be established based on an equipment calibration routine at installation.

Neural network (specifically Long Short-Term Networks) and deep learning models are continually updated with time series inputs of labeled activities, mobility measures, discovered activities sequences, and vital signs. These models identify significant changes in these inputs over time, allowing the recognition of anomalous activity on the part of the monitored individual. This anomaly recognition serves as the basis for prediction of chronic disease exacerbation/health status and decline.

To train classification algorithms, the variables are assigned into labeled and unlabeled buckets and the machine learns from the data lake that originates from over one million observations. The model applies classification algorithms, neural networks, and deep learning in a large data lake comprised of one million+ ground truth observations for disease prediction on 200 homes. These algorithms are distinct due to the nature of the data source that predicts a highly validated activities of daily living of a human subject along with RR/HR. It is unique to obtain one million observations on human subject's real core activities of daily living in order to train the machine to predict daily human activities. In a given sample demographics, the machine takes no more than 2 weeks of consecutive daily monitoring to train itself on a new home and individual making the replicability of the product very quick and therefore valuable.

Dashboards: FIG. 3 illustrates the methodology applied towards a layered process of dashboard accessibility to human subjects, doctors, nurses, caregivers, insurers, medical device controllers, chatbots, telehealth, home-healthcare services, and so forth. The dashboard 310 is programmed to be visually available and integrated into the clinical workflow process at nurse stations, EPIC and CERNER-GENESIS electronic health record systems and on mobile phone applications, wearables and smart speaker system. The system has an inbuilt crisis alert mechanism that is triggered into a red-amber-green signal to caregivers and clinical managers. This is dynamically programmed based on individual input into the settings of the dashboard. An example is a monitored individual does not eat for an entire day or uses the toilet several more times than usual in a day, thus triggering an amber alarm. Red would correspond to a scenario were contact needs to be made with the patient immediately. The data available on the dashboard 310 has several available time horizons depending upon the analysis required. For example, it is possible to seek the history and timings of toilet use over the past 30 or 60 days.

An amber alarm may be triggered when a score determined by the systems and methods described herein reaches a certain threshold. Likewise, red alarm may be triggered when the score determined by the systems and methods described herein reaches another threshold. All alarms may be audio and/or visual alarms. The alarms may be at the dashboard 310, or at a mobile device of a caregiver or relative of the patient.

Detecting declines in functional status and early indicators of chronic disease exacerbation in the home setting can provide the opportunity to intervene earlier to prevent accidents, complications, and more severe exacerbations. Such intervention has the potential to reduce patient morbidity and risk of mortality, decrease emergency department (ED) and hospital utilization, enhance assisted and senior living, and reduce system cost.

To continuously and objectively monitor chronic disease patients in their daily life requires an unobtrusive autonomous system in the home. In addition to primary effects of chronic disease, the systems and methods disclosed herein can also permit monitoring of adverse therapeutic drug effects and functioning of implantable medical devices such as heart pacemakers and neural stimulators through auxiliary sensors. This sensor configuration is enabled by the integration and interoperability of a set of collaborative sensors. The ability to unobtrusively and passively monitor chronic disease patients in the home offers the potential for earlier identification of exacerbations with less reliance on patient and senior living adherence and less patient burden. Beyond the ability to predict chronic disease exacerbations, tracking changes in daily activities of the elderly and those with some degree of cognitive impairment can allow family caregivers and providers to monitor the overall well-being of a patient and to identify areas where the individual is having difficulty safely performing the activities necessary for independent living.

The systems and methods described herein outline an exemplary process of a crisis event prediction model for COPD (chronic obstructive pulmonary disease), CHF (congestive heart failure), CLD (chronic liver disease), MCI (mild cognitive impairment) and multi-morbidity (multiple chronic conditions). In some embodiments, there are 17 elements (e.g. shown as the rows of FIG. 6, e.g., respiratory rate, heart rate, toilet flushes, and so forth) in the chronic disease crisis event prediction model that combine both activities of daily living and physiological conditions of the patients. Each of the five conditions has a distinct set of parameters that are monitored. Anomalies outside of normal ranges specific to a particular disease trigger early warning alerts based on the degree of warning that the system generates.

In the case of COPD (chronic obstructive pulmonary disease), when physiological conditions start to change i.e. respiratory rates increase, heart rate increases, body temperature increases and concurrently daily activities decline, the model generates an early alert based on the severity of the conditions. The model does not attribute any weight to toileting and the patient's body weight changes in relation to COPD conditions deteriorating.

In the case of CHF (congestive heart failure), the model is designed to evaluate changes to heart rate, body weight, toileting and sleeping. With the exception of walking, which will increase the other activities of daily living decline. These would also include a drop in IADLs (instrumental activities of daily living). In case the patient has implanted devices (e.g. pacemaker) device signals can be integrated and edge processed into the hub-data stream, and the system can act as a backup for heart rate monitoring in case of battery failure.

In the case of CLD (chronic liver disease), the model is designed to trigger an alert if there is a decrease in toileting and other common activities (e.g. cooking, performance of household chores, home-leaving) and a concurrent increase in respiratory and heart rate.

The case of MCI (mild cognitive impairment) and all conditions described above, the system evaluates overall activity levels and patterns (including regularity), mobility, and sleep.

Figure 6:
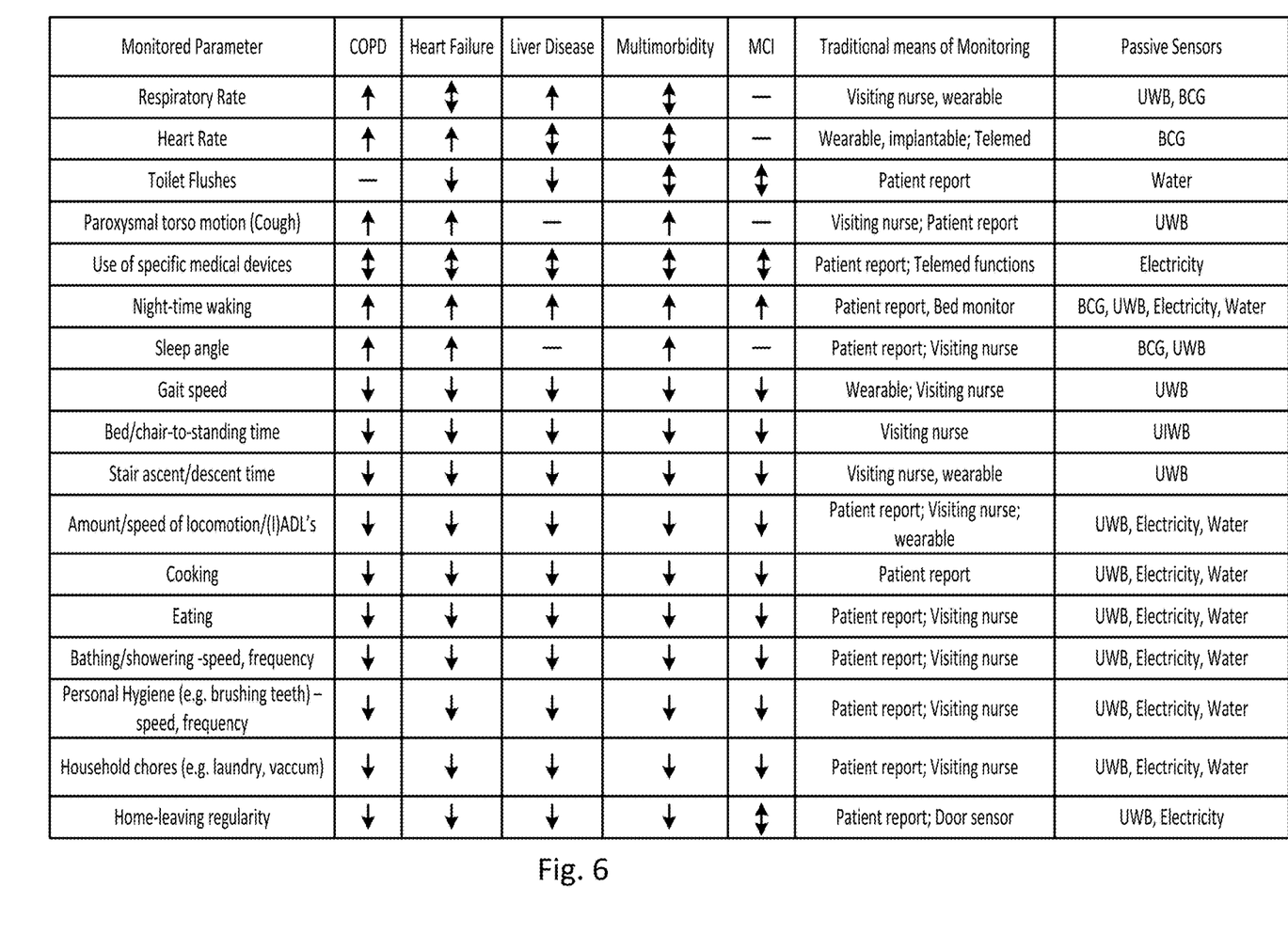
FIG. 6 illustrates changes in patterns of monitored parameters that characterize exacerbations of five common chronic conditions.

FIG. 6 shows typical patterns of change indicative of declining health status arising from five common conditions, which are integrated into the devices/systems/methods described herein. The FIG. 6 not a comprehensive model but a dynamic valid representation. For example, an up arrow (↑) in FIG. 6 means that an increase in a monitored parameter is associated with an increase in a probability of the crisis event. For instance, FIG. 6 shows that an increase in heart rate (HR) suggests higher probabilities of impending COPD or CHF exacerbation. Likewise, a down arrow (↓) in FIG. 6 means that a decrease in a monitored parameter is associated with an increase in probability of a crisis event. For instance, FIG. 6 shows that a decrease in cooking suggests a higher probability of any of the five illustrative conditions. Bidirectional arrows (↕) indicate that exacerbation of a given condition may be predicted by changes in either direction of the monitored parameter. For example, CHF exacerbation may be associated with either increase or decrease RR. Finally, a dash in FIG. 6 represents that a change in the monitored parameter has no relationship with the probability of the crisis event. For instance, an increase or decrease in toilet flushes has no association with the likelihood of COPD. Patterns of co-occurring changes in these 17 parameters (rows in FIG. 6) that are more consistent with one or more of the condition-specific profiles shown in FIG. 6 are weighted more heavily in the anomaly detection algorithms [232 of FIG. 2] which predict crisis events. However, a pattern of change does not have to be consistent with one of the condition-specific profiles in FIG. 6 to trigger an alert via an anomaly detection algorithm.

As the above makes clear, anywhere a dash appears in FIG. 6 represents that a change in the monitored parameter has no effect on the probability of the event. Thus, in some embodiments, when the probability of an event is calculated based on a score determined by the activity, the score will neither increase nor decrease for the dashed activities of FIG. 6 when the activity increases or decreases. For instance, for a score used to calculate a probability of liver disease, a patient's sleep angle will not have an effect on the calculated score.

With further reference to FIG. 6, it should be understood that UWB means Ultra wideband radar; and BCG means Ballistocardiography.

Of course, modifications and alterations will occur by others upon reading and understanding the preceding description. It is intended that the invention be construed as including all such modifications and alterations insofar as they come within the scope of the appended claims or the equivalents thereof.

The invention claimed is:

1. A system for producing an alarm for a prediction of chronic liver disease (CLD) for a patient, the system comprising:
an ultra-wideband (UWB) radar sensor;
a water censor configured to measure a water flow rate;
a dashboard configured to produce an audio or visual alarm;
at least one processor;
and at least one memory including computer program code;
the at least one memory and the computer program code configured to, with the at least one processor, cause the system at least to:
receive a measurement from the UWB radar sensor;
determine a respiratory rate of the patient from the measurement received from the UWB radar sensor;
receive a measurement from the water sensor;
determine a toileting activity of the patient based on the received measurement from the water sensor; and
trigger, at the dashboard, the audio or visual alarm of a prediction of exacerbation of CLD if there is a decrease in the toileting activity concurrent with an increase in the respiratory rate.

2. The system of claim 1, wherein the at least one memory and the computer program code are further configured to, with the at least one processor, cause the system to determine the toileting activity of the patient further based on: (i) ground truth observations, and (ii) training data from a home of the patient or from a population of patients.

3. The system of claim 1, further including:
a first electrical measurement device configured to measure an overall power usage of a home of the patient; and
a second electrical measurement device configured to measure a power usage of a kitchen of the home.

4. The system of claim 1, further including:
a first electrical measurement device configured to measure an overall power usage of a home of the patient, wherein the first electrical measurement includes a timestamp;
a second electrical measurement device configured to measure a power usage of a kitchen of the home, wherein the second electrical measurement includes a timestamp;
a sleeping sensor configured to measure sleep of the patient;
a vital sign sensor configured to measure a vital sign of the patient;
a mobility sensor configured to measure mobility of the patient; and
a presence sensor configured to measure a presence of the patient.

5. The system of claim 1,
wherein the at least one memory and the computer program code are further configured to, with the at least one processor, cause the system to predict a chronic obstructive pulmonary disease (COPD) event based on the respiratory rate of the patient but not the toileting activity of the patient.

6. The system of claim 1, wherein the at least one memory and the computer program code are further configured to, with the at least one processor, cause the system to predict the exacerbation of CLD further based on a gait speed of the patient but not a sleep angle of the patient.

7. The system of claim 1, wherein:
the at least one memory and the computer program code are further configured to, with the at least one processor, cause the system to receive one-way information from a medical device, and predict a chronic obstructive pulmonary disease (COPD) event based on the signal received from a medical device.

8. The system of claim 1, wherein:
the at least one memory and the computer program code are further configured to, with the at least one processor, cause the system to predict a congestive heart failure (CMF) event by applying an anomaly detection machine learning method to a signal received from a cardiac defibrillator or pacemaker.

9. The system of claim 1, wherein:
the at least one memory and the computer program code are further configured to, with the at least one processor, cause the system to predict the exacerbation of CLD further by applying an anomaly detection machine learning method to a signal of a liver stiffness or liver steatosis.

10. The system of claim 1, wherein
the at least one memory and the computer program code are further configured to, with the at least one processor, cause the system to detect increases in cognitive impairment event by applying an anomaly detection machine learning method to an integrated data stream from a neural stimulator device that stimulates brain memory function.

11. The system of claim 1, wherein
the at least one memory and the computer program code are further configured to, with the at least one processor, cause the system to predict a Multi-Comorbidity event by applying an anomaly detection machine learning method to a signal received from a medical device.

12. The system of claim 1, wherein the at least one memory and the computer program code are further configured to, with the at least one processor, cause the system to predict an event including chronic disease exacerbation or health status decline disease-agnostic.

13. The system of claim 1, further including a ballistocardiograph (BCG) measurement device.

14. The system of claim 1, wherein the UWB radar sensor is configured to make a presence measurement.

15. The system of claim 1, wherein the at least one memory and the computer program code are further configured to, with the at least one processor, cause the system to:
display an avatar of the patient on the dashboard; and
display a three-alarm system on the dashboard.

16. The system of claim 1, wherein the dashboard is configured to connect to end user health record systems and into mobile applications.

17. The system of claim 1, further comprising a hub configured for edge processing.

18. The system of claim 1, wherein the dashboard is configured to connect to a wearable.

19. The system of claim 1, wherein the dashboard is configured to connect to a smart speaker.

20. The system of claim 1, wherein the water sensor is an ultrasound water sensor.

21. The system of claim 1, wherein the prediction of the exacerbation of the CLD is based in part on a decrease in overall activity level and/or change in sleep pattern of the patient.

22. A method, comprising:
- with an ultra-wideband (UWB) radar sensor, taking a UWB radar measurement of a patient;
- receiving, with one or more processors, the UWB radar measurement from the UWB radar sensor;
- determining, with the one more processors, a respiratory rate of a patient from the UWB radar measurement;
- with a water sensor, taking a water measurement;
- receiving, with the one or more processors, the wafer measurement;
- determining, with the one or more processors, a toileting activity of the patient based on the received water measurement; and
- determining, with the one or more processors, that there has been a decrease in the toileting activity concurrent with an increase in the respiratory rate; and
- triggering, with the one or more professors and at a dashboard, an audio or visual alarm of a prediction oi exacerbation of chronic liver disease (CLD) in response to the determination that there has been a decrease in the toileting activity concurrent with an increase in the respiratory rate.

23. A system for producing an alarm for a prediction of chronic liver disease (CLD) for a patient, the system comprising:
- a sleep sensor including a ballistocardiograph (BCG) measurement device;
- a water sensor configured to measure a water flow rate;
- a dashboard configured to produce an audio or visual alarm;
- at least one processor;
- and at least one memory including computer program code;
- the at least one memory and the computer program code configured to, with the at least one processor, cause the system at least to:
- receive a measurement from the sleep sensor including the BCG measurement device;
- determine a respiratory rate of the patient from the measurement received from the sleep sensor including the BCG measurement device;
- receive a measurement from the water sensor;
- determine a toileting activity of the patient based on the received measurement from the water sensor; and
- trigger, at the dashboard, the audio or visual alarm of a prediction of exacerbation of CLD if there is a decrease in the toileting activity concurrent with an increase in the respiratory rate.

* * * * *